(12) United States Patent
Bessette

(10) Patent No.: US 6,506,707 B1
(45) Date of Patent: Jan. 14, 2003

(54) HERBICIDAL COMPOSITIONS CONTAINING PLANT ESSENTIAL OILS AND MIXTURES OR BLENDS THEREOF

(75) Inventor: Steven M. Bessette, Brentwood, TN (US)

(73) Assignee: Ecosmart Technologies, Inc., Franklin, TN (US)

( * ) Notice: Subject to any disclaimer, the term of this patent is extended or adjusted under 35 U.S.C. 154(b) by 0 days.

(21) Appl. No.: 09/517,620

(22) Filed: Mar. 3, 2000

Related U.S. Application Data

(60) Provisional application No. 60/123,174, filed on Mar. 5, 1999.

(51) Int. Cl.$^7$ .................... A01N 3/02; A01N 37/00; A01N 31/00
(52) U.S. Cl. .................... 504/116; 504/307; 504/354
(58) Field of Search .................... 504/127, 354

(56) References Cited

U.S. PATENT DOCUMENTS

| | | | |
|---|---|---|---|
| 4,759,930 A | | 7/1988 | Granirer et al. |
| 5,753,593 A | | 5/1998 | Pullen et al. |
| 5,935,905 A | * | 8/1999 | Mito .................... 504/128 |
| 6,020,287 A | * | 2/2000 | Brinker et al. .............. 504/116 |

FOREIGN PATENT DOCUMENTS

| | | | |
|---|---|---|---|
| BE | 1002598 | | 4/1991 |
| DE | 3733640 | | 4/1989 |
| DE | 4421471 | | 1/1996 |
| EP | 206987 | * | 12/1986 |
| EP | 0577914 | | 1/1994 |
| JP | 71034993 | * | 8/1968 |
| JP | 56120602 | * | 9/1981 |
| JP | 03 086802 | | 11/1991 |
| JP | 07087845 | * | 9/1995 |
| WO | WO8505038 | | 11/1985 |
| WO | WO9108670 | | 6/1991 |
| WO | WO 95/17822 | | 7/1995 |
| WO | WO 97/16975 | | 5/1997 |
| WO | 9827261 | * | 6/1998 |
| WO | WO 98/31223 | | 7/1998 |
| WO | WO9854971 | | 12/1998 |
| WO | WO9918802 | | 4/1999 |
| WO | WO 00/05964 | | 2/2000 |

OTHER PUBLICATIONS

Henzell, Phenol, an attractant for the male grass grub beetle, N.Z.J. Agr. Res., vol. 13(2), 294–6, 1970.*

Vaughn Steven, et al., "Volatile Monoterpenes as Potential Parent Structures for New Herbicides", *Chemical Astracts*, vol. 119, No. 7, Aug. 16, 1993.

Duke, Stephen, et al., "Terpenoids From the Genus Artemisia as Potential Pesticides", *Chemical Abstracts*, vol. 110, No. 19, May 8, 1989.

Dudai, N., et al., "Essential Oils as Allelochemicals and Their Potential Use a Bioherbicides", *Chemical Abstracts*, vol. 130, No. 25, Jun. 21, 1999.

"Toxicity and synergism of some plant extracts and insecticides against European corn borer egg–masses", Eldoksch, Hamdy et al., *Chemical Abstracts*, vol. 124, No. 19, May 6, 1996.

* cited by examiner

*Primary Examiner*—Alton Pryor
(74) *Attorney, Agent, or Firm*—McDermott, Will & Emery

(57) ABSTRACT

Herbicidal compositions containing plant essential oils and mixtures or blends thereof. In addition, the present invention is directed to a method for controlling weeds and grasses by applying a herbicidally-effective amount of the above herbicidal compositions to a locus where weed and grass control is desired.

9 Claims, No Drawings

HERBICIDAL COMPOSITIONS CONTAINING PLANT ESSENTIAL OILS AND MIXTURES OR BLENDS THEREOF

RELATED APPLICATION

This application is related to, and the benefit is claimed from, U.S. Provisional Application No. 60/123,174, which was filed on Mar. 5, 1999, the entire disclosure of which is incoporated herein by reference.

FIELD OF THE INVENTION

The present invention relates, in general, to herbicidal compositions containing plant essential oils and mixtures or blends thereof. In one aspect, the present invention relates to herbicidal compositions containing certain plant essential oils. In another aspect, the present invention relates to herbicidal compositions containing synergistic blends of certain plant essential oils. In a further aspect, the present invention relates to a method for controlling weeds and grasses by the application of pesticidally effective amounts of the herbicidal compositions containing certain plant essential oils and/or synergistic blends thereof to a locus where weed and grass control is desired.

BACKGROUND OF THE INVENTION

Weed and grass control is essential for, among other things, the efficient production of agricultural and horticultural crops, and herbicides are therefore the subject of extensive research and investigation. Weeds and grasses are problematic for many reasons, the end result of which is most often a reduction in the quantity and/or quality of the crop. Weeds and grasses compete with desired crops for water, nutrients, and sunlight, and can provide a refuge for insects and diseases that could damage the quality of the field. Weeds and grasses can also create problems in harvesting operations, and reduce the efficiency of the crop production. In household environments, weeds and grasses are also problematic. In addition to being a nuisance and eyesore in many situations, weeds and certain grasses can also compete with desired plants and grasses in turf and other lawn and garden environments. Herbicide applications for these environments will result in exposure to the general environment, including the water table, of residential and commercial settings.

The widespread use of herbicides has been around since 1940. However, it has become increasingly apparent that the widespread use of synthetic chemical herbicides has caused detrimental environmental effects that are harmful to humans and other animals. For instance, the public has become concerned about the amount of residual chemicals that persist in food, ground water and the environment, and that are toxic, carcinogenic or otherwise incompatible to humans, domestic animals and/or fish. Due to the fact that herbicides are applied to the soil and/or the foliar surfaces, they can easily reach streams, lakes, and reservoirs in water that runs off treated areas. As a result, many herbicide labels currently in use carry groundwater advisory statements regarding herbicide leaching. Worker safety is also an issue when applying these chemicals. Moreover, some target weeds and grasses have even shown an ability to develop immunity to many commonly used synthetic chemical herbicides. In recent times, regulatory guidelines have encouraged a search for potentially less dangerous herbicidal compositions via stringent restrictions on the use of certain synthetic herbicides. As a result, elimination of effective herbicides from the market has limited economical and effective options for controlling weeds and grasses. As an alternative, botanical herbicides are of great interest because they are natural herbicides, i.e., toxicants derived from plants that are safe to humans and the environment. It is also desirable to have botanical herbicides that are selective to certain weeds and grasses while permitting desirable grasses and other crops to flourish.

Accordingly, there is a great need for novel herbicidal compositions containing plant essential oils and synergistic mixtures thereof, especially those that are selective in nature. In addition, there is a need for methods for using same that address the problems described above, i.e., are safe to humans and the environment and relatively inexpensive to use in obtaining acceptable levels of weed and grass control.

SUMMARY OF THE INVENTION

A primary object of the present invention is to provide novel herbicidal compositions that contain certain plant essential oils.

Another object of the invention is to provide herbicidal compositions containing synergistic mixtures or blends of certain plant essential oils.

A still further object of the present invention is to provide a method for controlling weed and grass growth by the application of the compositions of the present invention to a locus where such control is desired.

It is a further object of the present invention to provide a fast-acting, rapid defoliant for pre-harvest applications.

It is a further object of the present invention to provide a selective herbicide that can be used to control certain weeds and grasses without affecting desirable plant matter.

It is still another object of the present invention to provide a novel herbicide that is safe and can be used in conjunction with conventional pesticides, including but not limited to herbicides e.g., glyphosate and 2, 4-D.

It is still another object of the present invention to provide a synergist for conventional herbicides, thereby providing quick burn down of plant matter coupled with systemic action on roots using lower rates of conventional pesticides.

It is still another object of the present invention to provide a non-systemic herbicide that can be used to remove green plant matter without affecting the stem of the plants.

It is a further object to provide a safe, non-toxic herbicidal composition and method that will not harm the environment.

It is a further object of the present invention to provide a novel herbicide that is comprised of food grade materials and is exempt from U.S. Environmental Protection Agency registration.

It is still another object of the present invention to provide a novel herbicide that is comprised of food grade materials and is exempt from tolerance under the U.S. Federal Food and Drug Cosmetic Act.

It is still another object to provide a herbicidal composition and method that has a pleasant scent and that can be applied without burdensome safety precautions.

It is still another object to provide a herbicidal composition and method as described above which can be inexpensively produced or employed.

It is yet another object of the invention to provide a herbicidal composition and method to which weeds and grasses cannot build immunity.

The above and other objects are accomplished by the present invention which is directed to herbicidal compositions containing certain plant essential oils and herbicidal compositions containing synergistic mixtures or blends of certain plant essential oils. In addition, the present invention is directed to a method for controlling weeds and grasses by applying a pesticidally-effective amount of the above herbicidal compositions to a locus where weed and grass control is desired.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety. In the case of inconsistencies, the present disclosure, including definitions, will prevail.

In one embodiment, the present invention provides a herbicidal composition comprising, in admixture with a suitable carrier and optionally with a suitable surface active agent, a plant essential oil compound and derivatives thereof, including racemic mixtures, enantiomers, diastereomers, hydrates, salts, solvates and metabolites, etc.

Each plant essential oil or derivative thereof, comprises a monocyclic, carbocyclic ring structure having six-members and substituted by at least one oxygenated or hydroxyl functional moiety. Examples of plant essential oils encompassed within the present invention, include, but are not limited to, members selected from the group consisting of aldehyde C16 (pure), amyl cinnamic aldehyde, amyl salicylate, anisic aldehyde, benzyl alcohol, benzyl acetate, cinnamaldehyde, cinnamic alcohol, α-terpineol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, d-limonene, menthol, methyl anthranilate, methyl ionone, methyl salicylate, α-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and the like. As these plant essential oil compounds are known and used for other uses, they may be prepared by a skilled artisan by employing known methods.

For example, a preferred embodiment relates to a herbicidal composition for agricultural and household use comprising a mixture of eugenol, alpha-terpineol, citronellal, thymol and trans-anethole.

Another preferred embodiment relates to herbicidal compositions for household use for i) broadleaf weed control or ii) total weed and grass control, comprising a mixture of eugenol and 2-phenethyl propionate at various dosage rates.

Another preferred embodiment relates to a herbicidal composition for agricultural and household use comprising a mixture of eugenol and 2-phenethyl propionate synergized by the addition of thymol.

It will be appreciated by the skilled artisan that the herbicidal compositions of the present invention unexpectedly exhibit excellent herbicidal activities without corresponding issues of toxicity to mankind and the environment. It will be further appreciated that the herbicidal compositions of the present invention provide unexpectedly fast action against green plant matter without systemic action against plant roots. Without wishing to be bound by the following theories, it is believed that plant essential oils disrupt cell membranes in plant tissue, releasing proteins within the plant matter. Alternatively, plant essential oils inhibit amino acid synthesis, and preclude production of certain enzymes which allows the plant cell to produce essential amino acids. Alternatively, plant essential oils may act as photosynthesis inhibitors or pigment inhibitors. Photosynthesis inhibitors prevent the plant's conversion of sunlight into chemical energy required for growth. Pigment inhibitors prevent production of certain plant pigments that are necessary for photosynthesis. In any event, the net effect of the toxicity and action of the inventive composition disclosed herein is heretofore unknown and unexpected.

Use of herbicidal compositions of the present invention generally results in fast, effective weed and grass control, particularly against broadleaf plants. As such, they are advantageously employed as herbicidal agents in uses such as, without limitation, agriculture, defoliants, organic farming, households, lawn and garden, professional pest control, foliage application, solid treatment, soil incorporation application, seedling box treatment, stalk injection and planting treatment, turf and ornamentals, etc.

With respect to agriculture, the compositions are so chemically inert that they are compatible with substantially any other constituents of the spray schedule. They may also be used in combination with other pesticidally active compounds, including other herbicides.

The term "carrier" as used herein means an inert or fluid material, which may be inorganic or organic and of synthetic or natural origin, with which the active compound is mixed or formulated to facilitate its application to the plant, seed, soil or other object to be treated, or its storage, transport and/or handling. In general, any of the materials customarily employed in formulating pesticides, herbicides, miticides or fungicides, are suitable. The inventive herbicidal compositions of the present invention may be employed alone or in the form of mixtures with such solid and/or liquid dispersible carrier vehicles and/or other known compatible active agents, especially plant protection agents, such as other pesticides, or insecticides, miticides, acaricides, nematicides, fungicides, bactericides, rodenticides, fertilizers, growth-regulating agents, etc., if desired, or in the form of particular dosage preparations for specific application made therefrom, such as solutions, emulsions, suspensions, powders, pastes, and granules which are thus ready for use. The herbicidal compositions of the present invention can be formulated or mixed with, if desired, conventional inert pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

Formulations containing the herbicidal compositions of the present invention may be prepared in any known manner, for instance with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the herbicidal compositions of the present invention. Generally, it is desirable to use as little of the agent as is possible, consistent with the desired dispersion of the herbicidal compositions of the present invention in the spray so that rain does not re-emulsify the herbicidal compositions of the present invention after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

Liquid concentrates may be prepared by dissolving a composition of the present invention with a solvent and dispersing the herbicidal compositions of the present inventions in water with the acid of suitable surface active emulsifying and dispersing agents. Examples of conventional carrier vehicles for this purpose include, but are not limited to, aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g. kaolins, clays, vermiculite, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.).

Surface-active agents, i.e., conventional carrier vehicle assistants, that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which act as carriers for the pesticide. These finely divided solids preferably have an average particle size of less than about 50 microns. Granules may comprise porous or nonporous particles. The granule particles are relatively large, a diameter of about 400–2500 microns typically. The particles are either impregnated or coated with the inventive herbicidal compositions from solution. Granules generally contain 0.05–25%, preferably 5–15%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

If desired, volatile organic compounds suitable as the fragrance ingredient for use in formulations for household applications, include, but are not limited to, amyl salicylate, citronellol, citronelloxyacetaldehyde, cyclamen aldehyde, citronellyl isobutyrate, coumarin, cyclohexyl acetate, cyclohexyl butyrate, diethyl malonate, ethyl 2-acetyl-5-ketohexanoate, isobornyl acetate, linalool, phenethyl alcohol, undecanol, alpha-hexylcinnamaldehyde, 2-methylhexanol, hexalon, phenylacetaldehyde, cis-3-hexen-1-ol, cyclamal, veronol, eugenol, Lyral, Galaxolide, Citralva, musk ambrette, terpinyl acetate, geraniol, alpha-damascone, alpha-methylionone, and the like. Illustrative of volatile essential oils are oil of Bergamot, cedar leaf, cedar wood, geranium, lavender, white cedar, sandalwood oil, rose extract, violet extract, galbanum oil, and the like. Synthetic types of organic fragrances are described in publications such as U.S. Pat. Nos. 4,314,915; 4,411,829; and 4,434,306.

In commercial or agricultural applications, the present invention encompasses carrier composition mixtures in which the herbicidal compositions are present in an amount substantially between about 0.01–95% by weight, and preferably 0.5–90% by weight, of the mixture, whereas carrier composition mixtures suitable for direct application or field application generally contemplate those in which the active compound is present in an amount substantially between about 0.0001–10%, preferably 1–5%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The herbicidal compositions can also be used in accordance with the so-called ultra-low-volume process, i.e. by applying such compounds or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed. In this process it is possible to use highly concentrated liquid compositions with said liquid carrier vehicles containing from about 20 to 95% by weight of the herbicidal compositions or even the 100% active substances alone, e.g. about 20–100% by weight of the herbicidal compositions. The mixture of active materials may be applied, without limitation, in sufficient amounts so as to provide about 0.2 to 4 and preferably about 1 to 2 pounds of active materials per acre. Moreover, the required amount of the herbicidal composition contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to 90 percent by weight. Satisfactory sprays, dusts, or granules for general use contain from about ¼ to 15 pounds of active herbicidal compositions per acre.

Furthermore, the present invention encompasses methods for killing, combating or controlling weeds and grasses, which comprises applying to at least one of correspondingly (a) such weeds and grasses and (b) the corresponding field, i.e. the locus to be protected, e.g. to a growing crop, to an area where a crop is to be grown, a correspondingly combative, a pesticidally effective amount, or toxic amount of the particular herbicidal compositions of the invention alone or together with a carrier as noted above. The instant formulations or compositions may be applied in any suitable usual manner, for instance by spraying, atomizing, vaporizing, scattering, dusting, watering, squirting, sprinkling, pouring, fumigating, and the like. The method for controlling weeds and grasses comprises applying the inventive composition, ordinarily in a formulation of one of the aforementioned types, to a locus or area to be protected from the weeds and grasses, such as the agricultural fields, turf and ornamentals, lawn and garden, rights of way, concrete pathways and driveways, etc. The compound, of course, is applied in an amount sufficient to effect the desired action. This dosage is dependent upon many factors, including the targeted plant, the selectivity desired, the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage with which the plant matter comes in contact—is of the order of 0.001 to 0.5% based on the total weight of the formulation, though under some circumstances the effective concentration will be as little as 0.0001% or as much as 25%, on the same basis.

The herbicidal compositions and methods of the present invention are effective against a wide variety of plant matter and it will be understood that the weeds and grasses exemplified and evaluated in the working Examples herein are representative of such a wider variety. The data and examples show that specific compounds are highly effective against broadleaf weeds, yet sensitive to narrow grasses and the like. In certain instances, specific compounds are highly effective against certain grasses while sensitive to other grasses.

The composition and method of the present invention will be further illustrated in the following, non-limiting Examples. The Examples are illustrative of various embodiments only and do not limit the claimed invention regarding the materials, conditions, weight ratios, process parameters and the like recited herein.

EXAMPLE 1

Herbicidal Effect of Plant Essential Oils and Mixtures or Blends Thereof Against Broadleaf Weeds and Grasses Studies were conducted to determine the herbicidal activity of a mixture of plant essential oils consisting of eugenol, thymol, trans-anethole, $\alpha$-terpineol and citronellal against a variety of broadleaf weeds and grasses. The mixture had the following ingredient ratios:

Eugenol (10%)
Thymol (40%)
Trans-Anethole (25%)
$\alpha$-Terpineol (10%)
Citronellal (15%)

The studies were performed at two urban locations In each instance, the mixture was placed, as is, into a handheld, pump sprayer. The sprayer was pressurized and the nozzle adjusted to a fine, cone-shaped spray pattern. The spray was applied to runoff and made in late afternoon. The spray was directed at weeds growing along the sidewalk where grasses were also present. In particular, the spray was directed at large dandelions and several small broadleaf weeds.

Within 30–60 minutes of treatment, the dandelion showed symptoms of distress. The leaves lost their rigidity and discoloration started to occur. Within 24 hours the dandelion was completely wilted and when sample foliage was hit with a low pressure stream of water, all the leaves separated from the stem, which would not occur with a healthy dandelion. Undisturbed dandelions became brown and withered away within a week.

The small broadleaf weeds along the curb became white and appeared to die within 5 days of treatment. The grassses along the curb, however, appeared to be unaffected.

Both tests indicate that the application of a spray containing plant essential oils and mixtures thereof resulted in a rapid damage of the leaves, resulting in the death of the green matter and elimination of the dandelion and other broadleaf weeds.

EXAMPLE 2

Herbicidal Effects of Plant Essential Oils and Mixtures or Blends Thereof Against Broadleaf Weeds and Grasses A multi-purpose field study was established on Jul. 28, 1998 and observed for four weeks, using a mixture of plant essential oils in water, the mixture consisting of eugenol, thymol, trans-anethole, $\alpha$-terpineol and citronellal. The mixture had the following ingredient ratios:

Eugenol (10%)
Thymol (40%)
Trans-Anethole (25%)
α-Terpineol (10%)
Citronellal (15%)

The product was applied broadcast in 20 gallons of total spray volume per acre at rates of 4.0, 2.0, 1.0, 0.5 and 0.25 gallons of plant essential oil mixture per acre. All treatments were applied with a $CO_2$ backpack sprayer equipped with a step log dilution apparatus and replicated twice.

The data clearly show that at rates above 0.25 gallons of plant essential oil mixture per acre, there was a significant phytotoxic activity on weed species in the plots. This demonstrated strong herbicidal activity appeared to be specific, but limited to, broadleaf species, including dandelions.

EXAMPLE 3

Herbicidal Effects of Plant Essential Oils and Mixtures or Blends Thereof Against Plant Matter Studies were conducted to determine the herbicidal activity of an aerosol mixture of plant essential oils consisting of eugenol, 2-phenethyl propionate, benzyl alcohol, and peppermint oil against a variety of broadleaf weeds and grasses.

The studies were conducted on a farm in Indiana by direct topical application. Applications were made at different times during the day, and therefore under different environmental conditions relating to humidity and temperature. Applications were made at 7:00 a.m., 12:00 p.m. and late afternoon. Multiple replicates were completed. Temperatures ranged from 61° F. to 90+° F.

The plants treated were the following:
Wild Mustard
Penny Smartweed
Ragweed, common and giant
Plantin
Crabgrass
Sourdock
Canadian Thistle
Soybean
Clover Certain trees such as volunteer oak were also treated to remove green matter. Vines within flower gardens were also treated.

The results indicate that the application of a spray containing plant essential oils and mixtures thereof resulted in rapid damage to all plant species, resulting in the death of the green matter.

The study further demonstrated that the green matter could be removed from the trees without damaging the tree itself. Also, the plant essential oils provided rapid and impressive control of the vines in the flower garden. The study concluded that the plant essential oils provided excellent herbicidal activity against plant matter with which they came into contact.

EXAMPLE 4

Herbicidal Effects of Plant Essential Oils and Mixtures or Blends Thereof Against Plant Matter Studies were conducted to determine the herbicidal activity of plant essential oils consisting of eugenol and 2-phenethyl propionate, and mixtures thereof, against a variety of weeds and grasses, under field and/or greenhouse conditions. A positive control (Roundup®) and a negative control were used. Four replicates were completed for each study, two studies were completed for each plant species. Plant damage was assessed as a damage rating on a scale of 0–5, with 5 being total damage. The essential oils were tested in water-based emulsions for all studies. Some studies included an aerosol formulation containing eugenol and 2-phenethyl propionate. The plants were sprayed to runoff and evaluated at 24 hours post treatment for damage ratings.

The plant essential oils were tested against the following plant materials:
Narrow Leaved Plantain (*Plantago lanceolata* L.)
Dandelion (*Taraxacum officinale* Weber )
Lamb's Quarters (*Chenopodium album* L.)
Redroot Pigweed (*Amaranthus retroflexus* L.)
Wild Oats (*Avena fatua* L.)
Barnyard Grass (*Echinochloa crusgalli* (L.) Beauv.)
Green Foxtail (*Setaria viridis* (L.) Beauv.)

The data and results indicate that the application of one or more plant essential oils provides rapid herbicidal action, within 24 hours. The results varied depending upon the plant species, but all experienced significant damage within 24 hours, predominantly ranked between 3–5 for damage. The aerosol formulations provided faster and more significant damage, possibly due to the action of the solvents in spreading across plant surfaces. The plant essential oils worked faster and better within 24–48 hours than the positive control, which claims a systemic action on roots. Some plants treated with the plant essential oils experienced minor regrowth over one to two weeks, but even the positive control did not provide total control of all plants over time. The plant essential oils are fast-acting herbicides that significantly damage plant matter. There was some variation between field and greenhouse conditions, possibly due to the effect of the environment on weakened plant materials. Plantain, dandelions, and lamb's quarters were particularly susceptible to the plant essential oils.

EXAMPLE 5

Toxicity of Various Plant Essential Oils to Cabbage

Various plant essential oils were tested for toxicity (herbicidal action) against greenhouse-grown cabbage leaves. Individual oils were ranked for relative toxicity using the direct droplet bioassay on the cabbage leaves. $EC_{50}$ values (amount producing 50% of maximum effect) were recorded in micrograms (all applied in one microliter of methanol) and plotted on a graph for comparison.

The plant essential oils tested were as follows:
Cinnamic Aldehyde
Cineole
Mentha Piperita
Phenethyl Alcohol
White Thymol
Methyl Salicylate
D-Pulegone
Trans-Anethole
(−) Terpinen-4-ol 97%
Pennyroyal
Citronellal
(+) Terpinen-4-ol 95%
Cinnamic Alcohol α-Terpineol Terpinen-4-ol The study clearly demonstrated that methyl salicylate, cinnamic aldehyde, white thymol, trans-anethole, pennyroyal, and citronellal were most toxic to cabbage leaves.

EXAMPLE 6

Toxicity of Various Plant Essential Oils to Dandelion

Various plant essential oils were tested for toxicity (herbicidal action) against dandelion. Individual oils were ranked for relative toxicity using the direct droplet bioassay on the dandelion. $EC_{50}$ values (amount producing 50% of maximum effect) were recorded in micrograms (all applied in one microliter of methanol) and plotted on a graph for comparison.

The plant essential oils tested were as follows:

Cinnamic Aldehyde

Cineole

Mentha Piperita

Phenethyl Alcohol

White Thymol

Methyl Salicylate

D-Pulegone

Trans-Anethole (−) Terpinen-4-ol 97%

Pennyroyal

Citronellal (+) Terpinen-4-ol 95%

Cinnamic Alcohol

αTerpineol

Terpinen-4-ol

The study clearly demonstrated that white thymol, cinnamic aldehyde, pennyroyal, methyl salicylate, cineole, pennyroyal, and citronellal were most toxic to dandelion. The study demonstrates the selectivity present in some plant essential oils, by comparison of cineole on cabbage versus dandelion. Cineole may be desirable for agricultural sprays where phytotoxicity on crops is an issue.

EXAMPLE 7

Synergistic Effect of Mixture of Plant Essential Oils to Cabbage

Various plant essential oils were tested for synergistic effects on the toxicity (herbicidal action) against greenhouse-grown cabbage leaves. Individual oils were ranked for relative toxicity using the direct droplet bioassay on the cabbage leaves, and compared to mixtures at different ratios. Individual $EC_{50}$ values (amount producing 50% of maximum effect) were recorded in micrograms (all applied in one microliter of methanol) and compared to $EC_{50}$ values for mixtures. The results are presented below:

| Plant Essential Oils | $EC_{50}$ |
| --- | --- |
| Thymol | 10.7 |
| Eugenol | 46.1 |
| Phenethyl Propionate (PEP) | 158.8 |
| Thymol + Eugenol (1:1, wt:wt) | 16.8 |
| Thymol + PEP (1:1, wt:wt) | 21.9 |
| Thymol + Eugenol + PEP (1:1:1, wt:wt:wt) | 33.7 |
| Eugenol + PEP (1:1, wt:wt) | 89.7 |

The data clearly demonstrate the synergistic effects of the mixtures of plant essential oils. The specific blend of these three plant essential oils will always create synergistic action in terms of toxicity, but the individual plant essential oils, the blends thereof, and the ratio of the oils to each other in the blend will vary depending upon the plant species. This type of synergistic action permits efficient and economical applications.

EXAMPLE 8

Synergistic Effect of Mixture of Plant Essential Oils with Conventional Herbicides Various plant essential oils were tested for synergistic effects when used in combination with conventional herbicides. A eugenol/phenethyl propionate blend was added to Roundup® at 50:50 wt:wt, and applied to broadleaf weeds at the stated rate for Roundup®, effectively applying half the rate of both the eugenol/phenethyl propionate blend and Roundup®. The weeds were examined at 24 hours and one week and evaluated for damage and regrowth. The synergistic mixture provided rapid herbicidal action within 24 hours, and no observed regrowth occurred within one week. This data demonstrates that these safe, plant essential oils can be used in combination with conventional herbicides, thereby creating enhanced activity at lower effective rates.

As can be seen from the above discussion, the herbicidal compositions of active compounds according to the present invention are highly effective herbicides, but are much less toxic than known pesticidal agents/active compounds conventionally used for weed and grass control in the turf and ornamental, lawn and garden, household and agricultural markets. The pesticidal effectiveness of the particular new compositions of active compounds of the present invention is unexpected, given the nature of the plant essential oils and their safety.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method for controlling weeds and grasses, which comprises applying to the locus where control is desired a herbicidally-effective amount of a composition comprising, in admixture with an acceptable carrier a synergistic blend of, eugenol and 2-phenethyl propionate.

2. A method for controlling weeds and grasses, which comprises applying to the locus where control is desired a herbicidally-effective amount of a composition comprising, in admixture with an acceptable carrier a synergistic blend of, eugenol, 2-phenethyl propionate and thymol.

3. A method for controlling weeds and grasses, which comprises applying to the locus where control is desired a herbicidally-effective amount of a composition comprising, in admixture with an acceptable carrier a synergistic blend of, eugenol, thymol, trans-Anethole, α-Terpineol and citronellal.

4. A method for controlling weeds and grasses, which comprises applying to the locus where control is desired a herbicidally-effective amount of a composition consisting essentially of thymol in admixture with an acceptable carrier.

5. A method for controlling weeds and grasses, which comprises applying to the locus where control is desired a herbicidally-effective amount of a composition consisting essentially of phenethyl propionate in admixture with an acceptable carrier.

6. A method for controlling weeds and grasses, which comprises applying to the locus where control is desired a herbicidally-effective amount of a composition comprising, in admixture with an acceptable carrier, thymol and eugenol.

7. A method for controlling weeds and grasses, which comprises applying to the locus where control is desired a herbicidally-effective amount of a composition comprising, in admixture with an acceptable carrier a synergistic blend of, thymol and phenethyl propionate.

8. A method for controlling weeds and grasses, which comprises applying to the locus where control is desired a herbicidally-effective amount of a composition comprising, in admixture with an acceptable carrier a synergistic blend of, thymol, eugenol and phenethyl propionate.

9. A method for controlling weeds and grasses, which comprises applying to the locus where control is desired a herbicidally-effective amount of a composition comprising, in admixture with an acceptable carrier a synergistic blend of, eugenol and phenethyl propionate.

* * * * *